United States Patent
Hammer

(10) Patent No.: US 7,030,979 B2
(45) Date of Patent: Apr. 18, 2006

(54) MICROWAVE PLASMA SOURCE

(75) Inventor: Michael R. Hammer, Sassafras (AU)

(73) Assignee: Varian Austrailia PTY LTD, Mulgrave (AU)

( * ) Notice: Subject to any disclaimer, the term of this patent is extended or adjusted under 35 U.S.C. 154(b) by 64 days.

(21) Appl. No.: 10/502,927

(22) PCT Filed: Aug. 23, 2002

(86) PCT No.: PCT/AU02/01142

§ 371 (c)(1),
(2), (4) Date: Jul. 28, 2004

(87) PCT Pub. No.: WO03/069964

PCT Pub. Date: Aug. 21, 2003

(65) Prior Publication Data

US 2005/0078309 A1     Apr. 14, 2005

(30) Foreign Application Priority Data

Feb. 11, 2002  (AU) ..................................... PS0442

(51) Int. Cl.
*G01N 21/73* (2006.01)

(52) U.S. Cl. .................................. 356/316; 219/121.48

(58) Field of Classification Search ................ 356/316; 219/121.48
See application file for complete search history.

(56) References Cited

U.S. PATENT DOCUMENTS

| | | |
|---|---|---|
| 4,933,650 A | 6/1990 | Okamoto |
| 5,051,557 A | 9/1991 | Satzger |
| 5,235,401 A | 8/1993 | Cilia et al. |
| 5,302,803 A | 4/1994 | Stevens et al. |

FOREIGN PATENT DOCUMENTS

WO      WO 02/04930 A1      1/2002

*Primary Examiner*—F. L. Evans
(74) *Attorney, Agent, or Firm*—Bella Fishman

(57) ABSTRACT

A plasma source for a spectrometer includes a plasma torch (10) located within a waveguide or resonant cavity (40) for both the electric and the magnetic field components of a microwave electromagnetic field to excite a plasma (54). This produces a plasma (54) having a generally elliptical cross section into which sample is relatively easily injected but which still provides good thermal coupling between the plasma and the sample. The invention gives significantly improved limits of detection compared to prior art microwave induced plasma systems. The torch is preferably axially aligned with the direction of the magnetic field component and may be located within a resonant iris (32) within the waveguide or cavity (40).

13 Claims, 3 Drawing Sheets

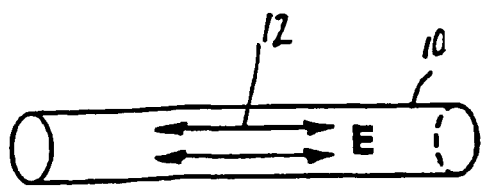  
FIG 1a  FIG 1b  FIG 1c
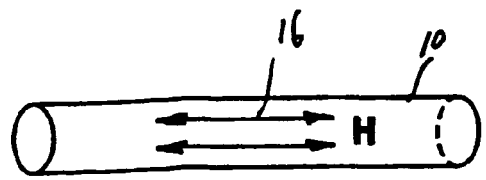  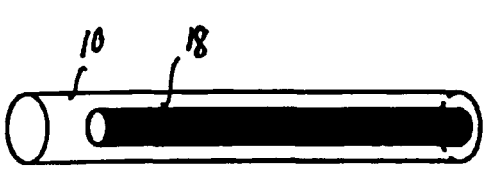
FIG 1d  FIG 1e  FIG 1f
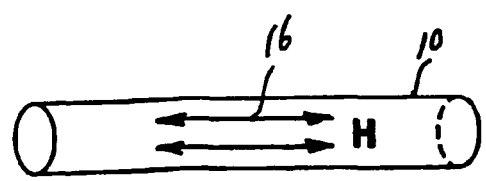  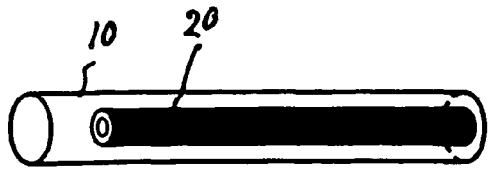
FIG 1g  FIG 1h  FIG 1i
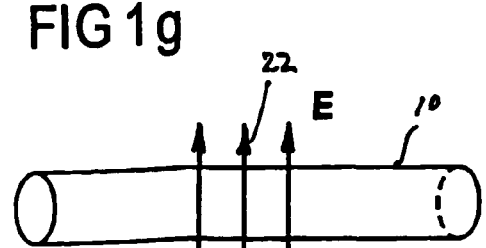  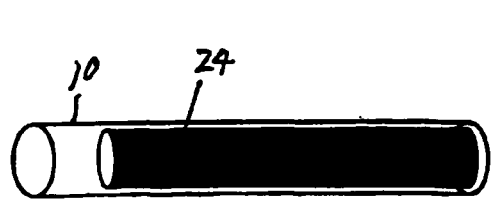
FIG 1j  FIG 1k  FIG 1l
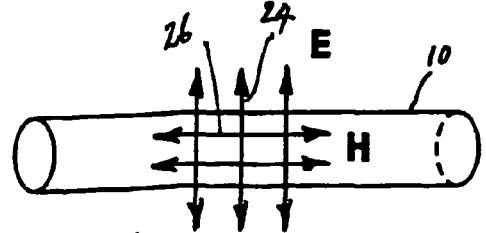  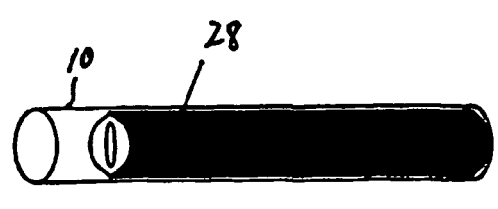
FIG 1m  FIG 1n  FIG 1o

MICROWAVE PLASMA SOURCE

TECHNICAL FIELD

The present invention relates to means for producing a plasma by microwave power for heating a sample for spectrochemical analysis, for example by optical emission spectrometry or mass spectrometry.

BACKGROUND

The applicant's prior International Patent Application No. PCT/AU01/00805 (WO 02/04930 A1) discloses axially aligning a plasma torch with the magnetic field maximum of an applied microwave electromagnetic field for excitation of a plasma. This induces a hollow generally circular cylindrical shaped plasma due to the well known "skin effect". A plasma of this shape is desirable because it is easier to inject a sample into its cooler core for heating. The skin depth of this plasma, which decreases at increased frequencies, is quite thin (for example, at 2455 MHz the skin depth of an argon plasma has been measured as about 1 mm) and thus use of a polyatomic plasma forming gas (which gives a greater skin depth) is disclosed to improve the heating into the core region of the plasma for heating sample within that region.

Further research by the applicant has revealed that improved results are obtained compared to the invention of PCT/AU01/00805 by energising the plasma by simultaneous application of an electric and a magnetic field oscillating at microwave frequency. The improved results flow from better heating into the core region of the plasma and thus better thermal coupling between the sample and the plasma leading to improved analytical performance (sensitivity).

The discussion herein of the background to the invention is included to explain the context of the invention. This is not to be taken as an admission that any of the material referred to was published, known or part of the common general knowledge in Australia as at the priority date established by the present application.

SUMMARY OF THE INVENTION

According to a first aspect of the present invention there is provided a plasma source for a spectrometer including
  a plasma torch having at least one passage for supply of a plasma forming gas,
  means for applying a microwave electromagnetic field to the plasma torch,
  said means being associated with the torch for both the electric and the magnetic field components of the applied microwave electromagnetic field to excite a plasma of the plasma forming gas.

Also, according to a second aspect, the invention provides a method of producing a plasma for spectrochemical analysis of a sample including relatively locating a plasma torch within a microwave electromagnetic field for both the electric and the magnetic field components of the microwave electromagnetic field to be applied to the plasma torch for both field components simultaneously to excite a plasma in a plasma forming gas flowing through the torch.

In both aspects of the invention, the plasma torch is located in a region where electric and magnetic fields exist. This can be achieved by positioning the torch at an intermediate position between electric and magnetic field maxima within a waveguide. Alternatively it may be achieved by positioning the torch within a resonant structure such as an iris. Such a structure provides a local maximum for both electric and magnetic fields. In either case, both the electric and the magnetic field components of the applied microwave power contribute towards sustaining the plasma.

The effect of the electric field component is for the plasma to adopt the shape of a ribbon aligned with the electric field direction and the effect of the magnetic field component is for the plasma to adopt a hollow cylindrical shape. The combination of the two orthogonal field components causes the hollow cylindrical shape (from the magnetic field component) to become generally elliptical in cross section and for the plasma to extend into the core region but at a lower intensity compared to the outer regions. Thus a plasma torch of the apparatus or method aspects of the invention can be selectively located within a microwave electromagnetic field such that the relative intensities of the electric and magnetic field components will give a desired lower level of plasma intensity in the core compared to the skin region of the plasma, that is, to give a reduced core intensity sufficient to allow injection of the sample therein, but which is still sufficiently high as to give good excitation of the sample for good analytical results.

Preferably the plasma torch is axially aligned with the magnetic field. This preferred arrangement with the torch axially aligned to the magnetic field component means that the direction of the electric field component will be orthogonal or transverse to the axis of the torch. With this arrangement, the electric field produces a plasma in the form of a "band" (that is, like an axially extending strip having a narrow cross section). The magnetic field causes the band cross section to divide into two and form a narrow ellipse when viewed end on. Adjustment of the relative intensities of the two field components (for example, by placing the torch in different locations within the microwave electromagnetic field inside a cavity) widens or narrows the gap between the two sides of the band forming the ellipse and thus allows optimisation of the trade-off between the ability to inject sample into the plasma yet still achieve good thermal coupling between the plasma and the sample.

Preferably the means for applying a microwave electromagnetic field to the torch includes a resonant iris within which the torch is located. Choice of the relative intensity of each field component is achievable by changing the relative height to width ratio of the iris opening, such change still retaining overall resonance at the frequency of the applied microwave energy.

Alternatively or additionally, the means for applying the microwave electromagnetic field may be, or may include, a waveguide or a cavity within which the torch is located partway between the position of an electric field maximum and the position of a magnetic field maximum within the waveguide or cavity. Suitable cavities are disclosed in the above mentioned PCT/AU01/00805. For example, the plasma torch can be positioned within a cavity formed from a one-wavelength long section of waveguide partway between the position of maximum magnetic field strength and the position of maximum electric field strength. Changing the position of the plasma torch between these two field maximums allows choice of the relative intensity of each field component and thus of the elliptical cross sectional shape of the plasma and thus of the plasma core intensity.

Where the means for applying the microwave electromagnetic field is a cavity, preferably a microwave source (for example a magnetron) provides the microwave energy directly into the cavity, the torch (that is, the plasma load) also being positioned within the cavity. This avoids a usual prior art set up wherein a microwave generator (typically a magnetron) is positioned in a launch waveguide and impedance matched to a feeder waveguide or coaxial cable used to conduct the microwave energy to the load, in this case the plasma torch, with said load commonly being additionally impedance matched to the feeder waveguide or coaxial cable. This feature of the invention avoids the requirement for one or two extra impedance matching networks, which would otherwise add to the size and expense of the overall system. A possible arrangement according to the invention is to form a cavity from a length of waveguide short-circuited at both ends and to have a magnetron mounted onto this length of waveguide in a conventional manner. Matching the real component of impedance between the magnetron and plasma is achieved by controlling the distance between the magnetron and the plasma torch. Cancelling out the reactive impedance including the magnetron reactance is achieved by controlling the distance from the magnetron to the near short-circuited end. The exact distances required can be determined either by trial and error or by use of a microwave network analyser as would be known by a person skilled in the art. In practice, the optimal magnetron position has been found to be quite close to a low impedance point (close to half a wavelength from the torch position). Thus the matching requirements will determine to some degree the overall length of the cavity. It has also been found in practice that variations in torch impedance with different power levels or sample flows are not large enough to significantly affect the impedance match achieved by the above process and thus dynamic adjustment of impedance matching is not required.

Another aspect of this invention relates to the thermal cooling of a cavity for applying the microwave electromagnetic field to the torch. Considerable power is dissipated within the plasma torch and the torch and a cavity within which it is positioned will most probably need to be cooled. According to this aspect of the invention, any such cavity may be used as a cooling duct. Thus cooling air may be introduced into the cavity and extracted by tubes having a diameter that is below cut-off for the microwave frequency being employed and whose length is sufficient to attenuate the evanescent wave to an acceptable degree.

For a better understanding of the invention and to show how the same may be carried into effect, preferred embodiments thereof will now be described, by way of non-limiting example only, with reference to the accompanying drawings.

BRIEF DESCRIPTION OF DRAWINGS

FIGS. 1a to 1o schematically illustrate field directions and resultant plasma shapes for a plasma torch.

DESCRIPTION OF PREFERRED EMBODIMENTS

Figure 3:
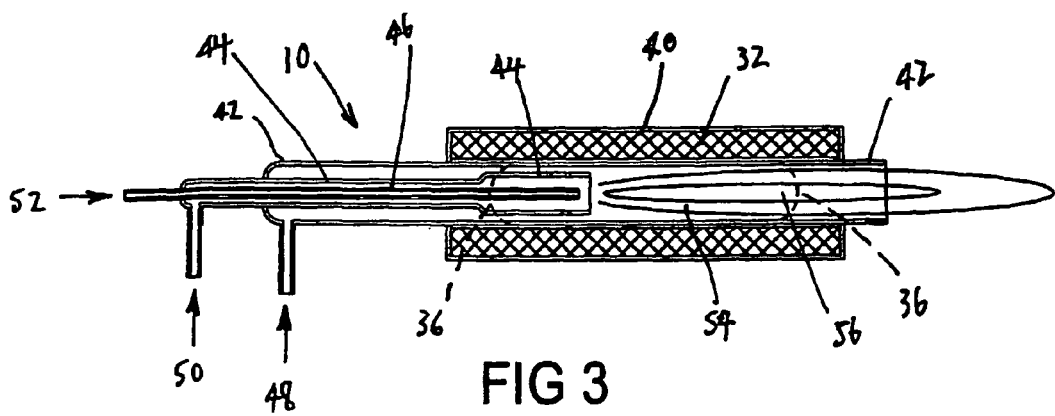
FIG. 3 is a cross-sectional view of a plasma torch within a resonant iris within a waveguide according to an embodiment of the invention.
Figure 4:
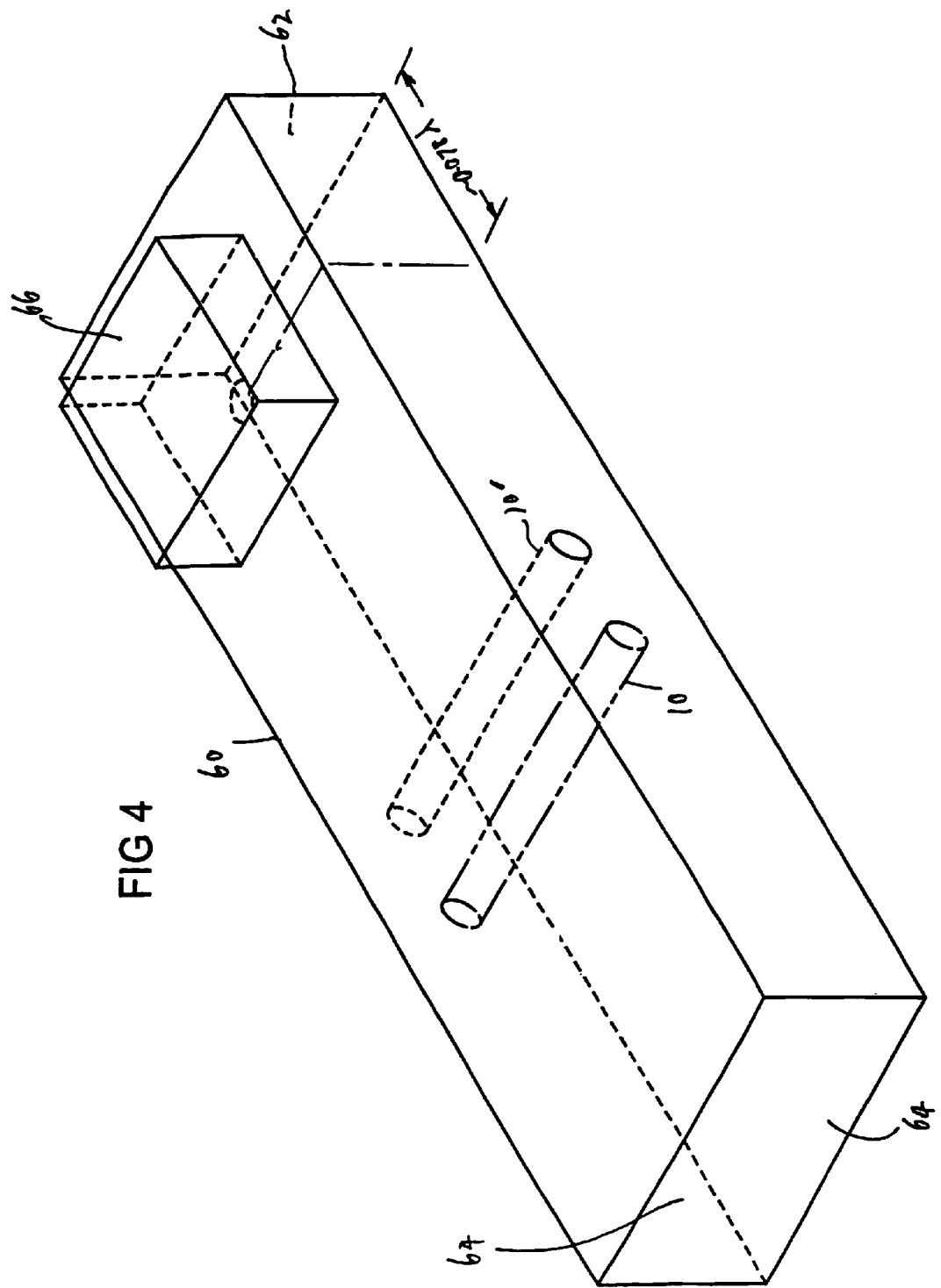
FIG. 4 schematically illustrates a cavity for a plasma torch according to an embodiment of the invention and that the torch therein may be located in different positions.

FIGS. 1a, d, g, j and m illustrate electric E and magnetic H field directions relative to a plasma torch 10 (shown schematically as a cylinder) the fields being such as to excite a plasma in a plasma forming gas flowing through the torch 10. The plasma torch 10 is only diagrammatically represented in the figures as a cylinder because plasma torch structures for spectrometers are well known. Commonly in plasma torches at least two concentric tubes (typically of quartz) are used. A carrier gas with entrained sample normally flows through the innermost tube and a separate plasma sustaining and torch cooling gas flows in the gap between the two tubes. Typically the plasma forming and sustaining gas will be an inert gas such as argon or nitrogen and arrangements are provided for producing a flow of this gas conducive to forming a stable plasma having a hollow core, and to keeping the plasma sufficiently isolated from any part of the torch so that no part of the torch is overheated. For example, the flow may be injected radially off axis so that the flow spirals. This latter gas flow sustains the plasma and the sample carried in the inner gas flow is heated by radiation and conduction from the plasma. An example of a suitable plasma torch is described in detail herein below with reference to FIG. 3. FIGS. 1b, e, h, k and n illustrate plasma shapes looking into the end of the torch 10, and FIGS. 1c, f, i, l and o are side views (showing the same plane as FIGS. 1a, d, g, j and m, for example the figures are both vertical elevations) of the plasma shape.

FIGS. 1a, b and c show that for a microwave electromagnetic field with the electric field component 12 aligned axially of the torch 10, a rod-shaped plasma 14 is produced. This is the accepted approach and the plasma 14 that is produced is very hot but unfortunately it is extremely difficult to inject sample into the core of the plasma. As a consequence it is difficult to obtain good thermal coupling between the plasma 14 and the sample resulting in poor heating of the sample and thus poor analytical performance.

FIGS. 1d, e and f and FIGS. 1g, h and i show that when the plasma torch 10 is axially aligned with the magnetic field component 16 at the magnetic field maximum of an electromagnetic field (as in PCT/AU01/00805), the plasma shape is a hollow generally right circular cylinder. In FIG. 1e the right circular cylindrical plasma 18 is thin walled, as occurs with argon as the plasma forming gas. That is, the skin depth becomes so small that the central core of the plasma is not merely reduced in temperature but may in fact be relatively cold. Whilst it is easy to inject sample into such a core region, there is little heating and thus very poor analytical sensitivity. In FIG. 1h the generally circular cylindrical plasma 20 has a thicker skin depth as occurs with nitrogen as the plasma forming gas. However there is still insufficient heating of a sample within the core region of plasma 20 to give satisfactory analytical results.

FIG. 1j illustrates that for a transverse electric field 22, a band shaped plasma 24 is produced. With reference to FIG. 1m when a microwave electromagnetic field is applied such that both its electric 24 and its magnetic field 26 components provide energy to excite the plasma, with a magnetic field component 26 axially aligned with the torch 10, a generally elliptical cross-section shaped plasma 28 is produced. It is part of the invention that by selectively locating a plasma torch 10 within a microwave electromagnetic field such that the relative intensities of the electric 24 and magnetic field 26 components are at desired levels, the shape of the elliptical cross-section can be selected as will allow a desired balance between the degree of heating of sample within the core of the plasma and ease of injection of the sample therein.

Figure 2:
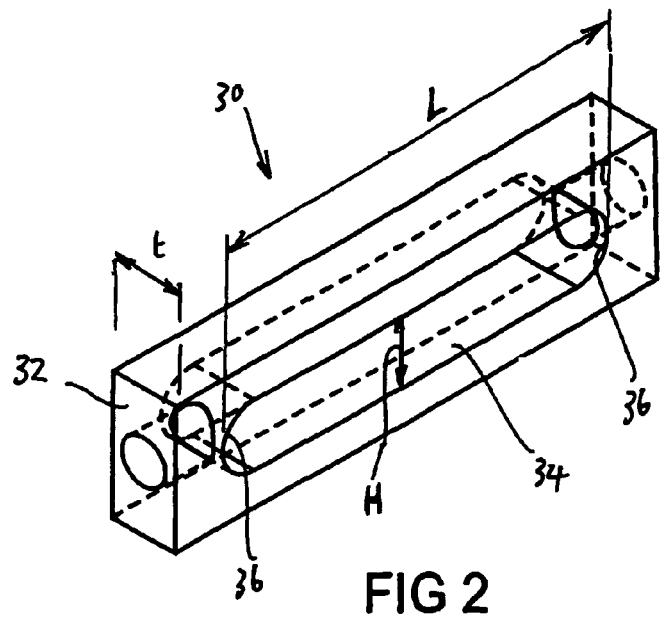
FIG. 2 illustrates a resonant iris for use in an embodiment of the invention.

With reference to FIG. 2, a resonant iris 30 for accommodating a plasma torch 10 may be made of a metal section 32 having an opening 34. This iris may be placed within a waveguide wherein the width and height of the waveguide at the resonant iris are simultaneously reduced. The reduced height represents a capacitor and the reduced width represents an inductor. The combination of a parallel inductor and capacitor forms a resonant circuit. The approximate conditions for resonance are that the perimeter of the opening 34 forming iris 30 be an integral number of half-wavelengths long. This is only approximate because the resonant frequency also depends on the thickness t of the section 32 (that is, its dimension along a waveguide). In practice the most expedient method of finding the exact size required is to make a trial opening with the perimeter of the opening n half-wavelengths long, where n is an integer, measure the exact resonant frequency and then linearly scale the length L or height H of the opening 34 to the exact frequency required. Ideally, such an opening should not have sharp corners since these cause undesirable field and surface current concentrations. A solution to this is to make the ends 36 of the opening 34 either radiused or semicircular. A ratio which has proven to be acceptable when using nitrogen as the support gas is a length L 2.6 times the height H, although it is to be understood that other ratios may also be effective both when using nitrogen as the plasma forming gas or when other plasma forming gases are used.

A plasma torch 10 for use in the invention may be similar to a known "mini torch" used for ICP applications, except for its outer tube being extended in length. Thus a torch 10 (illustrated in FIG. 3 as accommodated within a section 32 providing a resonant iris within a waveguide 40) consists of three concentric tubes 42, 44 and 46. Tube 42 is the outer tube, tube 44 the intermediate tube and tube 46 the inner tube. Tube 44 includes an end portion of larger diameter to provide a narrow annular gap between tubes 42 and 44 for the passage of plasma forming gas that is supplied through an inlet 48. The narrow gap imparts a desirably high velocity to the plasma forming gas. An auxiliary gas flow is supplied to tube 44 through an inlet 50 and serves to keep a plasma 54 formed from the plasma forming gas an appropriate distance away from the nearby ends of tubes 44 and 46 so that those ends do not overheat. A carrier gas containing entrained sample aerosol is supplied to inner tube 46 through an inlet 52 and on exiting the outlet of tube 46 forms a channel 56 through plasma 54 for the sample aerosol to be vaporised, atomised and spectrochemically excited by the heat of the plasma 54. As is known, the diameter of inner tube 46 is chosen to match the rate of flow of carrier gas and entrained sample aerosol provided by a nebuliser (or other sample introduction means) that is used with the torch 10. The velocity of the aerosol laden carrier gas emerging from inner tube 46 must be sufficient to make a channel 56 through the plasma 54, but not so great that there is insufficient time for the aerosol to be properly vaporised, atomised and spectrochemically excited. It has been found that a nebuliser and spray chamber from a conventional inductively coupled argon plasma system performs satisfactorily with the present invention when the internal diameter of tube 44 of a torch 10 is in the range 1.5–2.5 mm.

Torch 10 may be constructed of fused quartz and have an outer diameter of approximately 12.5 mm. Its outer tube 42 may be extended in length to protrude a short distance from a waveguide 40. FIG. 3 shows a torch in which the three tubes 42, 44 and 46 are permanently fused together, however a mechanical arrangement may be provided whereby the three tubes are held in their required positions wherein one or more of the tubes can be removed and replaced, as is known. Such an arrangement is called a demountable torch. Torch 10 may be constructed of materials other than quartz, such as for example alumina, boron nitride or other heat resistant ceramics. An embodiment as in FIG. 3 readily supports an analytically useful plasma in a plasma forming gas at power levels ranging from below about 200 watts to beyond 1 kW.

FIG. 4 shows a waveguide 60 which is short circuited at both ends 62, 64 and dimensioned to provide a resonant cavity within which a plasma torch 10 (shown only schematically in this Fig.) is located. A magnetron 66 is arranged to launch the microwave energy directly into the cavity 60 at a low impedance position, that is, close to a position of maximum magnetic field strength, with end 64 one wavelength (λ) from this position and with end 62 adjusted so as to cancel out the magnetron reactance (for example, end 62 may be approximately 0.078 λ from the magnetron 66). In this arrangement, waveguide cavity 60 operates in the $TE_{10n}$ mode (where n is an integer that depends on cavity length) with the torch 10 axially aligned with the direction of the magnetic field component. The plasma torch 10 is located such that a plasma is excited by both the magnetic and electric field components. The relative intensities of each component can be changed by changing the location of the torch 10, as represented by 10'. This has the effect, as explained hereinbefore, of altering the shape of the elliptical plasma produced by both the electric and magnetic field excitation components, thus allowing optimisation of the trade off between the ability to inject sample into the plasma and good thermal coupling between the plasma and sample.

Experimental Results

Probably the closest prior art to the present invention (and generally considered the best prior art microwave plasma system) is the system developed by Okamoto in Japan. (Yukio Okamoto, "Annular-shaped microwave induced nitrogen plasma at atmospheric pressure for emission spectroscopy of solutions", Analytical Sciences, 7(1991) 283–288; Yukio Okamoto, U.S. Pat. No. 4,933,650 (Jun. 12, 1990) and Yukio Okamoto, U.S. Pat. No. 5,063,329 (Nov. 5, 1991)). This is a nitrogen-based microwave plasma system running at a power of about 1 kilowatt. Sample introduction is via wet (undesolvated) aerosol from a pneumatic nebulizer. The analytical performance of an Okamoto system for emission spectroscopy is presented by Ohata and Furuta (Masaki Ohata and Naoki Furuta, "Evaluation of the detection capability of a high power nitrogen microwave-induced plasma for both atomic emission and mass spectrometry", Journal of Analytical Atomic Spectroscopy, 13 (1998) 447–453) Typical results reported are shown in Table 1 below.

TABLE 1

| ELEMENT | LIMIT OF DETECTION micrograms/liter |
|---|---|
| Aluminium | 12 |
| Arsenic | 840 |
| Cadmium | 24 |
| Copper | 2.3 |
| Manganese | 12 |
| Molybdenum | 180 |
| Lead | 80 |
| Selenium | 430 |
| Zinc | 50 |

For comparison, experimentally measured limits of detection for an optical spectroscopy system that utilises the present invention are shown below in Table 2. The optical spectrometer used was a Varian Vista MPX polychromator. This is an 0.5 meter echelle polychromator with a 20 picometer bandpass. The microwave cavity as described earlier was positioned in the location usually occupied by the conventional inductively coupled plasma torch. The microwave power was 1 kilowatt. Outer gas flow was 15 l/min with the intermediate and sample gas flow rates being approximately 1 l/min each.

TABLE 2

| ELEMENT | LIMIT OF DETECTION micrograms/liter |
|---|---|
| Aluminium | 0.28 |
| Arsenic | 140 |
| Cadmium | 9.6 |
| Copper | 1.3 |
| Manganese | 4.2 |
| Molybdenum | 2.0 |
| Lead | 5.0 |
| Selenium | 67 |
| Zinc | 12 |

As is evident from a comparison of the results in Tables 1 and 2, use of the present invention offers considerably lower limits of detection compared to the Okamoto prior art system.

In addition, the present invention offers the potential of operating on air, albeit with somewhat poorer (i.e. higher) limits of detection. This offers the considerable benefit of eliminating the need for any bottled gas supply. This advantage is particularly important in cases where the spectrometer instrument is operated in remote locations such as mining sites or in countries where bottled gas supply may be difficult to obtain. Limits of detection for some elements were determined for such a regime and are shown in Table 3 below.

TABLE 3

| Element | Emission line, nm | Limit of detection, micrograms/liter |
|---|---|---|
| Aluminium | 396.152 | 0.54 |
| Barium | 455.783 | 0.59 |
| Cadmium | 228.803 | 67 |
| Copper | 324.754 | 2.1 |
| Nickel | 341.482 | 5.6 |
| Lead | 405.783 | 21 |
| Strontium | 421.552 | 2.1 |

The invention described herein is susceptible to variations, modifications and/or additions other than those specifically described and it is to be understood that the invention includes all such variations, modifications and/or additions which fall within the scope of the following claims.

What is claimed is:

1. A plasma source for a spectrometer including
   a plasma torch having at least one passage for supply of a plasma forming gas,
   means for applying a microwave electromagnetic field to the plasma torch,
   said means being associated with the torch for both the electric and the magnetic field components of the applied microwave electromagnetic field to excite a plasma of the plasma forming gas.

2. A plasma source as claimed in claim 1 wherein the plasma torch has a longitudinal axis that is axially aligned with the direction of the magnetic field component.

3. A plasma source as claimed in claim 2 where in the means for applying a microwave electromagnetic field includes a waveguide.

4. A plasma source as claimed in claim 3 wherein the means for applying a microwave electromagnetic field includes a resonant iris within which the plasma torch is located, the resonant iris being located within the waveguide.

5. A plasma source as claimed in claim 4 wherein the resonant iris is located close to a magnetic field maximum or low impedance point within the waveguide.

6. A plasma source as claimed in claim 3, wherein the waveguide is a resonant cavity.

7. A plasma source as claimed in claim 6 wherein the means for applying a microwave electromagnetic field further includes a microwave source that supplies the microwave energy directly into the resonant cavity.

8. A plasma source as claimed in claim 7 wherein the microwave source is a magnetron.

9. A plasma source as claimed in claim 3 including means for introducing and extracting a gaseous coolant into and from the waveguide or resonant cavity whereby the waveguide or resonant cavity provides a duct for the coolant.

10. A method of producing a plasma for spectrochemical analysis of a sample including relatively locating a plasma torch within a microwave electromagnetic field for both the electric and the magnetic field components of the microwave electromagnetic field to be applied to the plasma torch for both the field components simultaneously to excite a plasma in a plasma forming gas flowing through the torch.

11. A method as claimed in claim 10, wherein the step of relatively locating includes axially aligning the torch with the direction of the magnetic field component.

12. A method as claimed in claim 11 wherein the step of relatively locating includes positioning the torch partway between the position of a magnetic field maximum and the positions of an electric field maximum.

13. A method as claimed in claim 12 wherein the plasma torch is located such that the electric and magnetic field components form a plasma of generally elliptical cross section.

* * * * *